(12) United States Patent
Yadav et al.

(10) Patent No.: US 6,946,197 B2
(45) Date of Patent: Sep. 20, 2005

(54) SEMICONDUCTOR AND DEVICE NANOTECHNOLOGY AND METHODS FOR THEIR MANUFACTURE

(75) Inventors: Tapesh Yadav, Niwot, CO (US); Dmitri Routkevitch, Longmont, CO (US); Peter Mardilovich, Corvallis, OR (US); Alex Govyadinov, Corvallis, OR (US); Stephanie Hooker, Longmont, CO (US); Stephen S. Williams, Longmont, CO (US)

(73) Assignee: NanoProducts Corporation, Longmont, CO (US)

( * ) Notice: Subject to any disclaimer, the term of this patent is extended or adjusted under 35 U.S.C. 154(b) by 3 days.

(21) Appl. No.: 10/783,629

(22) Filed: Feb. 20, 2004

(65) Prior Publication Data

US 2004/0161949 A1 Aug. 19, 2004

Related U.S. Application Data

(60) Continuation-in-part of application No. 09/996,471, filed on Nov. 27, 2001, now Pat. No. 6,713,176, which is a continuation of application No. 10/004,258, filed on Oct. 24, 2001, now Pat. No. 6,705,152, which is a division of application No. 09/274,517, filed on Mar. 23, 1999, now Pat. No. 6,344,271.

(60) Provisional application No. 60/242,905, filed on Oct. 24, 2000, provisional application No. 60/111,442, filed on Dec. 8, 1998, and provisional application No. 60/107,318, filed on Nov. 6, 1998.

(51) Int. Cl.$^7$ ............................................. B32B 5/16
(52) U.S. Cl. ..................... 428/402; 75/765; 423/276; 423/351; 423/414; 423/579
(58) Field of Search ........................ 428/402; 75/765; 423/276, 351, 414, 579

*Primary Examiner*—Long Pham
(74) *Attorney, Agent, or Firm*—Stuart T. Langley; Hogan & Hartson L.L.P.

(57) ABSTRACT

Device nanotechnology based on silicon wafers and other substrates is described. Methods for preparing such devices are discussed. The teachings allow integration of current semiconductor device, sensor device and other device fabrication methods with nanotechnology. Integration of nanotubes and nanowires to wafers is discussed. Sensors, electronics, biomedical and other devices are presented.

19 Claims, 7 Drawing Sheets

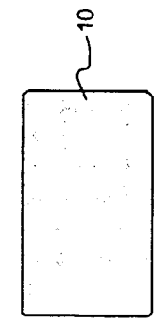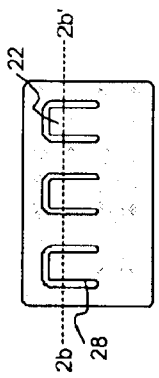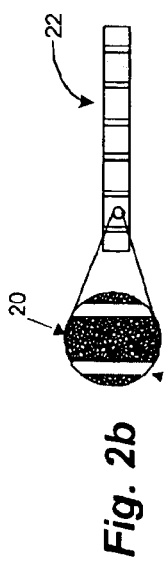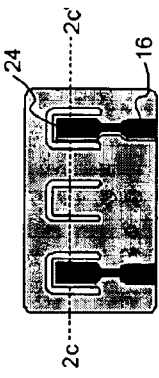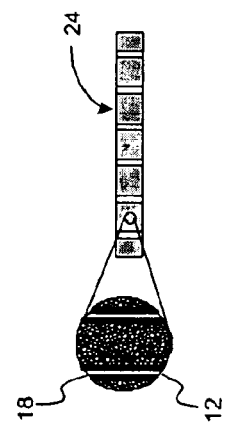

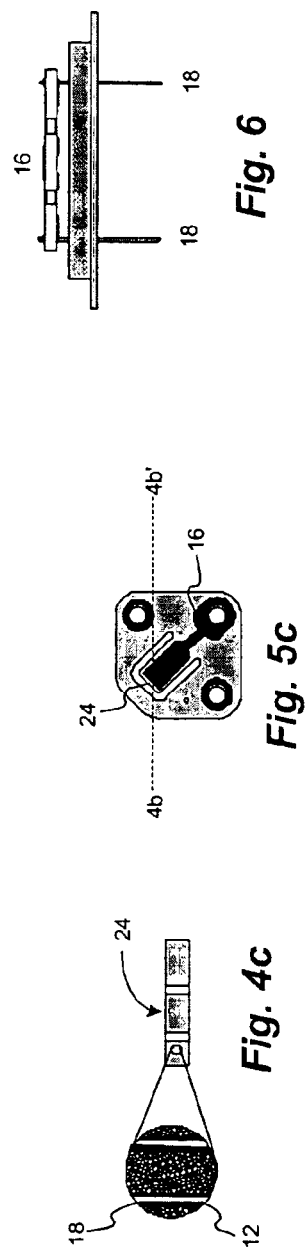
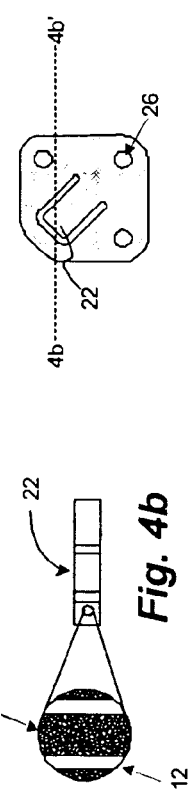
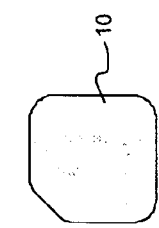
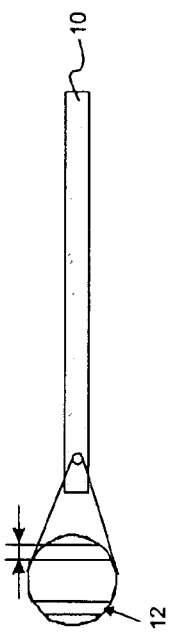
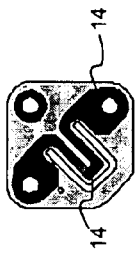
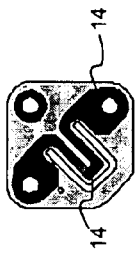

SEMICONDUCTOR AND DEVICE NANOTECHNOLOGY AND METHODS FOR THEIR MANUFACTURE

CROSS REFERENCE TO RELATED APPLICATIONS

This application is a continuation of patent application Ser. No. 10/004,258 filed on Oct. 24, 2001, now U.S. Pat. No. 6,705,152, which claims benefit to provisional U.S. patent application Ser. No. 60/242,905 filed Oct. 24, 2000, the disclosures of which are herein specifically incorporated by this reference. This application is also a continuation-in-part of patent application Ser. No. 09/996,471 filed on Nov. 27, 2001, now U.S. Pat. No. 6,713,176 entitled "PROCESSING AND MANUFACTURING METHODS ENABLED USING NON-STOICHIOMETRIC NANOMATERIALS" which is a Division of Ser. No. 09/274,517, filed Mar. 23, 1999 now U.S. Pat. No. 6,344,271, which claims benefit of Provisional Application No. 60/107,318 filed Nov. 6, 1998 and Provisional Application No. 60/111,442 filed Dec. 8, 1998 the disclosures of which are herein specifically incorporated by this reference.

STATEMENT REGARDING FEDERALLY SPONSORED RESEARCH

This invention was made under the funding by Small Business Innovative Research Program, contract numbers: 9960397 (NSF), DE-FG03-99ER82842 and DE-FG03-99ER82839 (DOE), R43 ES 10739 ZRG1 (NIH).

FIELD OF THE INVENTION

This invention relates to the nanostructured ceramic platform for design, methods of manufacture, operation modes, and uses of micromachined devices and device arrays in general, and sensors and sensor array devices in particular.

BACKGROUND OF THE INVENTION

The ability to monitor the chemical composition and physical parameters of gaseous environments, including indoor air quality, atmospheric measurements for weather forecasting, worker safety in hazardous environments and closed spaces, processing gases, and vehicle and plant exhaust, has been an important goal for several reasons. For example, the detrimental environmental effects of toxic species such as formaldehyde, carbon monoxide, ozone, hydrocarbons, chlorocarbons, nitrogen oxides and aromatics have led to the need to develop efficient, sensitive, and affordable ways of detecting the composition and presence of such toxic substances. Additionally, the efficiency of chemical processes, in terms of energy and raw material used per unit product or service delivered, relies on the ability to reliably sense deviations from the optimal processing conditions. Development of measurement and control technologies, including advanced sensor technology, is a critical component for lowering raw materials and energy consumption, improving the productivity and reducing generation of waste and pollutants. On the other hand, a primary concern for health care facilities as well as for other work place environments, are volatile organic compounds, such as alcohols, chlorinated hydrocarbons, aromatic solvents, and formaldehyde. Furthermore, humidity, temperature, and pressure are important environmental factors, which are of importance to both human comfort and to many industries and technologies, such as the production of electronic devices, precision instruments, food products, agriculture, horticulture, green houses and meteorology. Low-cost, light-weight sensors for routine balloon-borne measurements of water vapor concentration are required to provide one percent accuracy with high time resolution measurements at altitudes up to 20 km, low vapor concentration, and at temperatures down to at least minus 60° C.

Although physical, chemical, and biochemical sensing have been extensively researched, real-time monitoring and control leaves much to be desired. The following sensor performance parameters are in need of improvement for many applications: reliability and robustness, miniaturability, real time response, sensitivity and selectivity, built-in self-calibration, survivability in harsh application environments, low cost and manufacturability. Existing sensors have several inherent limitations that limit their performance, the most restraining are: cost, lack of selectivity, low reliability and durability, slow response, false response, the need for significant power, resistance to poisoning by sulfur-containing compounds and instability (hysteresis).

Existing approaches for high temperature microsensors are based mainly on planar technologies: the functional components (sensitive element, electrodes, temperature sensor, heating structures, and passivation) are made using standard thin or thick film deposition. Although significant breakthroughs were achieved in the development and fabrication of thin film microsensors, their performance parameters, especially sensitivity, reliability and working temperature range, still limits their usability. Moreover, portable sensor arrays capable of detecting multiple toxic air pollutants, such as volatile organics, carbon monoxide, formaldehyde, nitrogen oxides, and other air components, such as carbon dioxide and humidity are not available.

Recent advances in nanotechnology can greatly improve the sensor performance due to the possibility of tailoring the microstructure and chemistry at the nanoscale level, thus enhancing the gas-solid interaction. Although significant progress was achieved in different types of microsensors, synthesis of nanostructured high surface area sensing elements on intrinsically flat non-porous micromachined substrates is still a problem. Thin film microsensors fabricated on diaphragms, which are thermally decoupled from the substrate, demonstrated significant advantages in response time, and potential for array integration in comparison with larger (thick film) sensors. Nevertheless, there are several outstanding problems with existing thin film sensors. Small amounts and low surface area of sensitive material leads to lower signal-to-noise ratio (sensitivity), and easy loss of sensitivity on exposure to sulfur-containing compounds, as well as poor overall durability.

Nanostructured materials, with their small grain size, large number of grain boundaries and high specific area present new opportunities for the development and the commercialization of the next generation of gas sensors for air quality monitoring and control with significantly improved properties. The main challenge in realizing such opportunities is tailoring the sensing materials morphology and the composition at the nanometer scale. Furthermore, it is important that the nanostructured sensing element is manufactured in a form that is amenable to sensing device architectures and with ppb reproducibility.

If these issues were resolved, significant performance advantages could be realized. Low thermal mass and fast response microsensors could allow real time process monitoring and control, as well as will enable implementation of programmable temperature/voltage modulation for higher sensitivity and stability, elimination of drift and noise, and self-calibration. This invention addresses this opportunity.

Prior publications related to producing gas sensors include those of U.S. Pat. No. 4,631,952 which teaches a method of preparing a sensor by the formation of a dispersion of conducting particles with a material capable of swelling in the presence of the liquid, gas or vapor to be sensed. U.S. Pat. No. 4,984,446 teaches the preparation of a gas detecting device by a layer by layer build up process, and U.S. Pat. No. 4,988,539 teaches an evaporation-deposition method and process for manufacturing a gas detection sensor. U.S. Pat. No. 5,387,462 teaches a method of making a sensor for gas, vapor, and liquid from a composite article with an electrically conductive surface having an array of whisker-like microstructures with an aspect ratio of 3:1 to 100:1. U.S. Pat. No. 5,345,213 teaches a method for fabrication of temperature-controlled micromachined arrays for chemical sensor fabrication and operation. Furthermore, U.S. Pat. No. 6,079,873 describes a microhotplate-based differential calorimeter for detecting gases and chemical reactions. Although these prior methods provide improved methods for producing sensors, there is still a need to develop sensors that are selective, sensitive to trace species, fast, small, accurate, reproducible, stable in extreme environments, durable, and finally affordable.

Prior publications relevant to nanoporous anodic alumina include U.S. Pat. Nos. 4,472,533; 5,174,883; 5,198,112; 5,202,290 and 5,581,091, which describe methods of depositing various materials inside the nanoscale pores of anodic alumina. Depending on the material deposited in the pores and the pore size, these materials were described as suitable for use as catalysts, microelectrodes, reverse osmosis membranes, or nanoelectric devices. However, none of these references describe the manufacture of nanotubes of sensing materials, nor do they suggest that gas sensing devices can be constructed by these methods.

SUMMARY OF THE INVENTION

This invention teaches novel nanoporous structures as a means for nanotechnology devices for preparing advanced nanotech devices.

In one aspect, the present invention involves a sensor or sensor array platform comprising a micromachined nanostructured anodic substrate, bulk nanostructured sensing element, thin film or bulk microheater, temperature detector and gas permeable sensing electrodes. In other embodiments microheater may be the temperature detector and one of the sensing electrodes. The sensor may include other layers, for example, insulating layers. The sensor may be partially or completely coated, for example to protect the electrodes from environmental damage. The interaction between the sensor and the analyte may be physical, chemical, electronic, electrical, magnetic, structural, thermal, optical, or their combination.

The invention also includes a method of producing nanoporous sensor substrates from anodic alumina, comprising the steps of anodizing aluminum metal, or aluminum films on a substrate. These substrates include metals, silicon wafers, glass, and polymers. Anodic alumina films may be micromachined to delineate the sensor or sensor array substrate. The chemistry of the nanoporous substrate may be modified by liquid- or gas-phase processes to yield desired properties. The substrate may be annealed to create desired surface chemistry and specific surface area.

The invention also comprises a method of producing nanostructured sensing element using deposition of materials inside the pores of anodic alumina. The method includes providing an alumina film having a plurality of elongated parallel pores, and depositing a sensing material in the pores, wherein the pores have an average diameter of 500 nm or less. The resulting nanostructured sensing element comprises one or more materials selected from the group consisting of metals, non-metals, oxides, salts, polymers, and other organic and inorganic compounds. The sensing material may be deposited in the pores, for instance, by electrodeposition, sol-gel processes, solution impregnation, spin-coating, spray-coating, gas phase physical deposition and chemical vapor deposition.

In another aspect, the invention comprises an array of nanotubes or nanowires having an average diameter of less than 500 nm, wherein the array exhibits a high sensitivity and selectivity for a physical property or analyte. The invention also comprises methods of making devices incorporating the arrays of nanowires or nanotubes. The device may comprise conductive material selected from the a number of materials, including the group consisting of gold, silver, platinum, palladium, aluminum, copper, nickel, and alloys thereof, and may be deposited thereof. The nanotechnology device can be formed by a wide variety of techniques, including vacuum thermal evaporation, DC and RF plasma sputtering, chemical vapor deposition, electrochemical deposition, electroless deposition, and screen printing.

DEFINITIONS OF THE INVENTION

"Sensitivity", as that term is used herein, is a dimensionless measure equal to the ratio of the change in a measured property to the original value of that property. For example, the sensitivity of a chemical sensor whose resistance is a function of chemical environment is defined as $((R_a-R_s)/R_a)$ where $R_a$ represents the resistance of the sensor in the absence of the sensed chemical species, and $R_s$ represents the resistance of the sensor in the presence of the sensed chemical species.

BRIEF DESCRIPTION OF THE DRAWINGS

The invention is described with reference to the several figures of the drawing, in which:

FIG. 2a through FIG. 2c illustrate cross sections of a sensor array device implementation at various stages in processing;

FIG. 3a–3c illustrate top planar views of the embodiment shown in FIG. 2a–2c;

FIG. 3d shows a bottom planar view of the embodiments shown in FIG. 2a–2c;

FIG. 4a through FIG. 4c illustrate cross sections of a unitary sensor device implementation at various stages in processing;

FIG. 5a–5c illustrate top planar views of the embodiment shown in FIG. 4a–4c;

FIG. 5d shows a bottom planar view of the embodiments shown in FIG. 4a–4c;

FIG. 6 depicts an example of an assembled sensor device in accordance with the present invention;

DETAILED DESCRIPTION OF THE EMBODIMENTS

Figure 1:
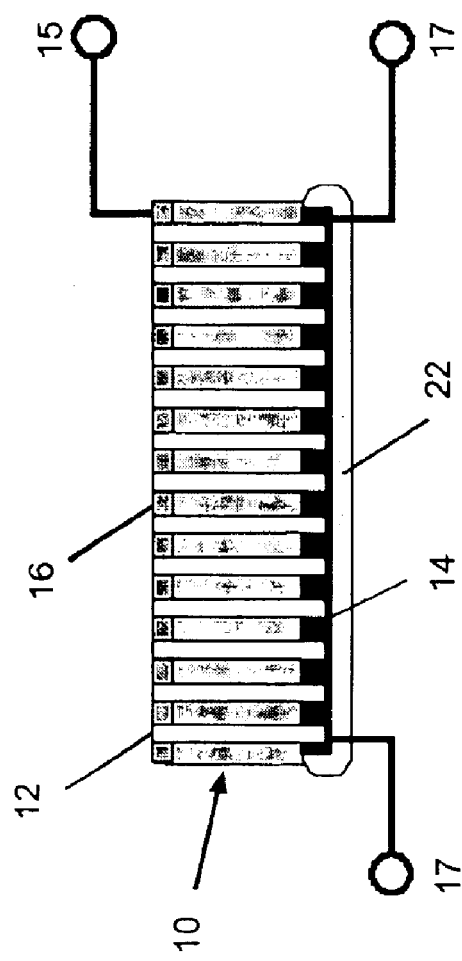
FIG. 1 depicts a generic diagram of nanostructured sensor platform according to the invention.

The subject of this invention is in the use of micromachined nanoporous anodic aluminum oxide (AAO) as a gas microsensor and microsensor array platform presented generally in FIG. 1. The nanoporous morphology of this material, as processed in accordance with the present invention, provides a desired ultra-high surface area and nanometer grain structure, therefore enabling high sensitivity. On the other hand, the refractory nature of alumina ceramic used in the specific embodiments enables desired robustness, long lifetime and stability in harsh environments.

"Sensitivity", as that term is used herein, is a dimensionless measure determined from the ratio of the change in a measured property to the original value of that property. For example, the sensitivity of a chemical sensor whose resistance is a function of chemical environment is defined as $((R_a-R_s)/R_a)$ where $R_a$ represents the resistance of the sensor in the absence of the sensed chemical species, and $R_s$ represents the resistance of the sensor in the presence of the sensed chemical species.

In addition to the general description presented with reference to FIG. 1, the present invention is described in terms of two particular embodiments. An array sensor process is shown in cross-section in FIG. 2a–FIG. 2c and in planar views in FIG. 3a through. FIG. 3d. A single device or unitary implementation is shown in cross-section in FIG. 4a–FIG. 4c and in planar views in FIG. 5a through FIG. 5c. For ease of illustration and understanding, analogous components of the different structures are labeled with similar identifying numbers.

Anodic alumina (AAO) substrate 10, as shown in FIGS. 1 and 2, comprises a high density of substantially uniform and substantially parallel nanosized pores 12, which are substantially perpendicular to the surface of the film. Once the raw substrate 10 is formed by etching, cutting, or other machining processes into a shape suitable for a sensor, it is referred to herein as a sensor substrate 22 as shown in FIGS. 2a–c, FIG. 3a–2, FIGS. 4a–c and FIGS. 5a–d. A highly anisotropic nanoporous morphology of AAO leads to the material exhibiting etching anisotropy, which may be used for micromachining sensor substrates and sensor array substrates 22. The nanoporous morphology of the AAO substrate is formed by electrochemical anodization of aluminum using electrolytes, which promote electric field assisted oxide dissolution. The particular examples described herein use an aluminum starting material, however, it is contemplated that other materials can be anodized to form a useful nanoporous morphology, including silicon, tantalum, and other materials and alloys. These are suitable alternatives in particular applications.

As shown in FIG. 1, a device is formed by providing electrodes 16 comprising a conductive material in electrical contact with sensor substrate and/or sensing element(s) 24 such that current flow through sensing element(s) 24 can be induced and measured. In the particular examples, resistivity changes in sensing element 24 produce a measurable response at measurement nodes or terminals 15 and 17. In preferred implementations, a microheater 14 is incorporated in an integrated fashion, e.g., on one surface of the sensing element 24, and powered by microheater power nodes 17 to implement a resistive heater. Microheater 14 is useful in operation to provide either pulsed or steady state heating of sensing element(s) 24. One aspect of the present invention also uses microheater 14 during manufacture or calibration of sensing element(s) 24 to implement "on-board" processing, such as anneal. Microheater 14 can efficiently provide heat to raise the temperature of sensor substrate 22 to temperatures in the range from ambient to 1200 C, which is a good working range for anneal processes that fine-tune the performance of sensing elements 24.

Diameter of nanopores 12 is tunable in the range from 1 to 500 nanometers by controlling the anodization conditions such as anodization current, anodization voltage, electrolyte concentration, anodization rate, and the like. Thickness of such films may be varied from 0.1 to 500 micrometers. Annealing of anodic alumina films leads to the formation of secondary pores 20 in the walls of the initial pores 12 as shown in FIG. 2b and FIG. 4b. Such annealing is performed, for example, using a thermal treatment ranging from 500 C to 1200 C in a forming gas, air, or oxygen containing environment. The formation of secondary pores 20 is accompanied by a sharp increase in specific surface area, chemical, thermal, and mechanical stability.

In overview, the methods of the invention comprise the following steps, illustrated in FIG. 2a–FIG. 2c, and FIG. 4a–FIG. 4c: growth of a nanoporous anodic alumina film 10 having elongated substantially parallel pores 12 of a desired size (FIG. 2a and FIG. 4a) micromachining of nanoporous alumina 10 to form a sensor or sensor array substrate 22 (FIG. 2b and FIG. 4b), selective etching of Al to separate the sensor substrates 22 from Al; post-anodization processing of anodic alumina to obtain desired phase composition, surface area and surface chemistry; deposition of sensing materials 18 in the pores to produce a nanostructured sensing element 24 (FIG. 2c and FIG. 4c); and deposition/patterning of thin films as electrodes 16, and microheaters 14 (FIG. 2d and FIG. 4d). Alternatively, a photoresist mask may be applied before anodization, and anodization may be performed in the openings of the mask to form sensor and sensor array substrates.

Growth of Nanoporous Anodic Alumina Substrates

In the growth of nanoporous anodic alumina, solutions of organic and inorganic acids, including but not limited to sulfuric acid, phosphoric acid, oxalic acid, chromic acid, boric acid, and citric acid, as well as their mixtures, may comprise the electrolyte. The electrolyte concentration preferably ranges from 0.1 to 99.9% by weight, more preferably 2 to 20% by weight. The temperature of the electrolyte preferably ranges from −90° C. to +150° C., more preferably from −20° C. to +35° C. The anodization voltage Ua preferably ranges from 0.5V to 500V, and more preferably from 5V to 100V.

Electrolyte, temperature and anodization voltage may be varied depending on the desired parameters of anodic alumina substrate, such as thickness, pore diameter, pore density, surface area, type and concentration of impurities. The pore diameter, for example, is observed to depend on the anodization voltage Ua. The pore density is observed to depend on the type of electrolyte used. The pore size is observed to decrease with decreasing Ua, and the film growth rate is observed to depend on the desired pore diameter and electrolyte composition, and is directly proportional to the current density. The film thickness is observed to be directly proportional to the charge density.

Aluminum foil or aluminum film on supporting substrates that preferably comprise at least 95% by weight aluminum, more preferably at least 99% by weight aluminum, and even more preferably at least 99.9% by weight aluminum, may be used for anodization. Prior to anodization, aluminum samples are preferably degreased and pressure annealed. Graphite, lead or aluminum plates may be used as counter electrodes. Anodization with constant voltage/current or with voltage/current modulated at high frequency may used to produce pores of diameter uniform throughout the thickness of the film. More complex process profiles of anodization voltage, current and/or temperature may also be used for the preparation of nanoporous alumina films. Changing process parameters at a low frequency (10 Hz and lower) may be used to fabricate pores with modulated diameter and density.

A dense oxide barrier layer normally separates the bottom of the pores from the underlying aluminum substrate. Anodic alumina substrates without this insulating layer may enhance sensor performance by allowing access of the gas from both sides of the sensing element. There are a variety of techniques for reducing and removing these insulation layers (also called barrier layers) from anodic alumina substrates including gradually reducing the cell voltage and then chemically dissolving the resulting thin barrier layer. The barrier layer in this case is pierced with small pores. This type of anodic alumina is referred to as "asymmetric" due to the different size of the pores at the top and bottom surfaces.

Yet another technique is to apply cathodic polarization to the aluminum substrate upon which the anodic alumina substrate is formed. Cathodic voltage or current may be less than, equal to or greater than the value of the anodization voltage and current. This cathodic polarization leads to rapid electrochemical dissolution of the barrier layer, and separation of the anodic alumina substrate from the aluminum substrate. These films have the same pore diameter at both faces and will be referred to as "symmetric". The electrolyte for this process may be the same as the anodization electrolyte or may be a different electrolyte preferably comprising strong acids. For example electrolytes are based on perchloric, acetic, and phosphoric acids and their mixtures can be used. A combination of these techniques can also be used.

Mixtures of perchloric and acetic acids are potentially explosive, so careful evaluation of safety issues and implementation of the safe handling procedures for this electrolyte are strongly advised.

Fabrication of Microsensor and Microsensor Array Substrates.

Microfabrication of sensor and sensor array device substrates from anodic alumina can be performed by anisotropic etching, localized anodization, or by combination thereof. In combination, these techniques enable versatile and flexible combination of bulk- and surface-like micromachining for gas sensors sensor arrays, and other ceramic microstructured and microdevices.

Figure 7:
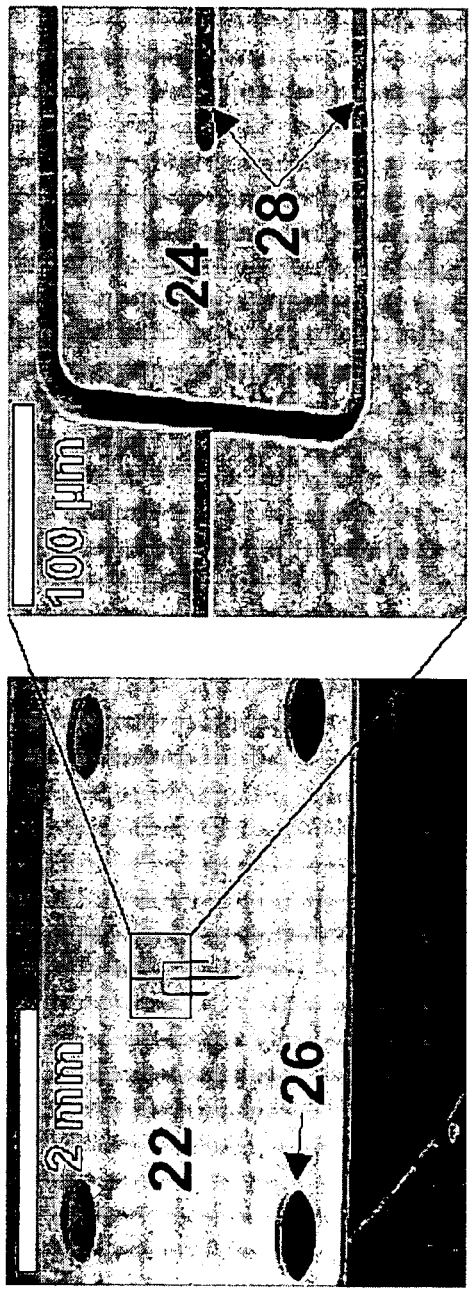
FIG. 7 shows a micrograph of ceramic sensor substrates produced by anisotropic etching as in Example 3.

The porous and compositional anisotropy of anodic alumina allows anisotropic etching of anodic alumina, with etchant species penetrating the entire thickness of the film and etching sideways. In one of the preferred implementations of this technique, the processing sequence comprises: (1) anodize Al to form nanoporous anodic alumina films of required thickness and morphology as described above; (2) deposit a protective thin film to close the pores to prevent the penetration of the photoresist deep inside the pores; this thin film preferably includes metals (such as aluminum, copper, nickel, molybdenum, tantalum, niobium, and their alloys), metal oxides, and other thin films; (3) apply and pre-bake a photoresist; (4) expose and develop the photoresist; (5) hard-bake photoresist pattern; (6) etch protective film; (7) anisotropically etch anodic alumina substrate in exposed areas of the film in the liquid or gas-phase process (preferably in the solution of phosphoric and chromic acids at temperature from 0° C. to 100° C., preferably from 50° C. to 95° C.); (8) strip photoresist and protective layers from resulting micromachined pattern; (9) separate sensor substrates from Al substrate by selective dissolution of Al; (10) rinse and dry resulting sensor substrates. This technique can be used for high aspect area ratio (up to 100:1) micromachining of anodic alumina films with resolution as low as 1 micrometer. A typical sensor substrate produced by this method is shown in the photomicrograph of FIG. 7.

Figure 8:
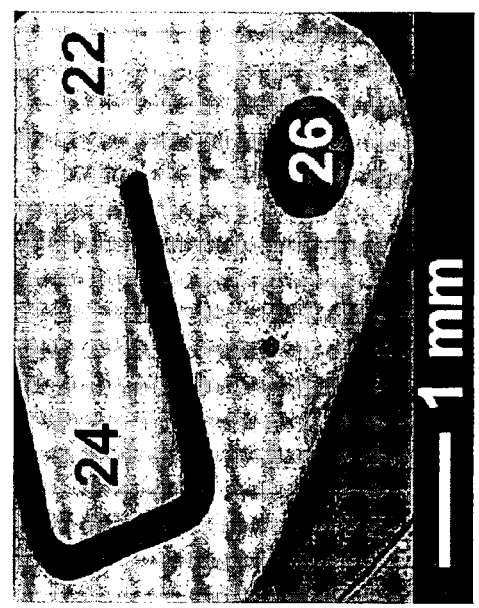
FIG. 8 shows a micrograph of ceramic sensor substrates produced by localized anodization as in Example 4.

In another approach, microsensor substrates from anodic alumina can be made by localized anodization, followed by selective etching of aluminum to release the resulting microstructure. This technique comprises the steps of: (1) pre-anodization of Al to form a thin layer (100–250 nm) of anodic alumina to increase the adhesion of the photoresist; (2) application of the photolithographic mask as described above; (3) anodization to form nanoporous anodic alumina sensor substrates of required thickness and morphology as described above; (4) strip photoresist and protective layers from resulting pattern; (5) separate sensor substrates from Al substrate by selective dissolution of Al. This technique can form sensor substrates with rounded edges, such as shown in the photomicrograph of FIG. 8 and is useful for low resolution microstructures with feature sizes over 10 $\mu$m. The main advantage of the microstructures produced by the method illustrated in FIG. 8 is that they may be mechanically stronger than the etched structure illustrated in FIG. 7.

According to the present invention, gas sensors and sensor array substrates comprise nanostructured ceramic dies of a particular shape. Two specific examples of are shown at various stages in processing in FIG. 3a–FIG. 3d and FIG. 5a–FIG. 5d. The sensor substrate can be formed into any desired shape including circular, elliptical, and polygonal. Depending on the packaging options, the die may or may not contain micromachined holes 26 for contact pins. In the particular examples, sensing elements 24 are preferably thermally decoupled from the rest of the die by micromachining them into a bridge-type or a cantilever-type structure, with optional thermal relief gaps 28 machined to relieve the thermal and mechanical stress caused by the operation of the microheater. The size of the die is preferably 0.1 mm to 200 mm, and more preferably from 2 to 20 mm, depending on the number of sensors in an array, the size of the package, and the size of the sensing element. The size of the sensing elements 24 along the largest dimension is preferably 0.005 mm to 100 mm, and more preferably 0.05 mm to 10 mm, depending on the sensor specifications, especially the desired power consumption. A plurality of sensing elements can be formed into an array (e.g., as shown in FIG. 3a through FIG. 3d).

The sensor substrate is preferably annealed to increase its surface area and chemical, mechanical and thermal stability. Annealing can be performed in air, preferably at temperatures greater than 500° C., and preferably in the range at 750° C. to 1200° C. The surface area of the resulting polycrystalline alumina is preferably up to 100 m2/g, more preferably 100 m2/g to 500 m2/g.

Electroding.

The nanoporous sensing elements are coupled to signal electrodes 16 deposited on one or both faces of the sensing element as shown in FIG. 3c (top plan view) and FIG. 3d (bottom plan view) of the array sensor implementation. The electrode deposition is also illustrated in plan views of FIGS. 5c and 5d in the single sensor implementation. To enable gas permeability, metal films of specific thickness are used, which are conductive but do not close the pores. The thickness of the gas permeable metal films can be in the range of 10 to 500 nanometers, depending on the pore diameter, a preferred thickness being in the range of 50 to 300 nm.

Temperature control of the sensing elements is enabled with thin film resistive microheaters 14. The thickness of thin film microheaters is preferably from 10 nm to 500 nm, more preferably 20 nm to 150 nm. The lateral dimensions of the microheater can be varied, depending on the size of the sensing element. Thickness, size and the material composition of microheater is tuned to obtain resistance preferably 2 $\Omega$ to 500 $\Omega$, more preferably 5 $\Omega$ to 100 $\Omega$.

In embodiments of this invention, a microheater may be also used as the temperature detector. A microheater can also be used as one of the sensing electrodes. In another preferred embodiment, the microheater may be separated from the sensing electrode by an insulating layer. The sensor may also be partially or completely coated to protect the electrodes from environmental damage.

In preferred embodiments, the electrode 16 and microheater 14, as shown in FIG. 3d and FIG. 5d, may comprise any composition that conducts the signal more easily than the sensing layer, and preferably with a lower impedance than the sensing layer. The composition of the electrode and microheater films preferably include inorganic materials, metallic, alloy, ceramic, non-metallic, ceramic-ceramic composite, ceramic-metal composite, metal-metal composite, and their combinations. In a preferred embodiment, an adhesion-promoting layer is deposited prior to the deposition of the sensing electrodes and microheaters.

Electrode geometries include porous or dense, flat or tapered, uniform or non-uniform, planar or wavy, straight or curved, non-patterned or patterned, grain size confined or not, and combinations of these geometries. Methods of forming the sensing electrodes and microheater include physical sputtering, reactive sputtering, physical vapor deposition, chemical vapor deposition, ion beam, e-beam deposition, molecular beam epitaxy, laser deposition, plasma deposition, electrochemical deposition, screen and stencil printing, brush painting, lift-off lithography, shadow mask deposition and combinations of these methods.

Prior to operating the sensor, the microheater may be pre-conditioned to stabilize its resistance by cycling the heater voltage from 0V (ambient) to an upper operating voltage limit for up to 1 week, more preferably for 15 to 60 minutes. The power consumption of the produced microsensors is preferably 1 mW to 1 W, more preferably 5 mW to 250 mW, for temperature of about 500° C.

Deposition of Sensitive Materials

Different materials can be deposited inside the pores of anodic alumina using a variety of processes, faithfully replicating its morphology. This will provide nanostructured, high surface area (up to 500 m2/g) sensitive elements 24 shown in FIG. 2c and FIG. 4c with higher signal-to-noise and improved performance in comparison with the planar substrates used in prior art thin film microsensors. In this embodiment of the present invention, the sensing materials can be deposited either before or after the microfabrication and electroding.

Methods of deposition of the sensing layer include spin coating, dip coating, spray coating, solution impregnation, physical sputtering, reactive sputtering, physical vapor deposition, chemical vapor deposition, atomic layer chemical vapor deposition via binary reaction sequences, ion beam, e-beam deposition, molecular beam epitaxy, laser deposition, plasma deposition, electrophoretic deposition, magnetophoretic deposition, thermophoretic deposition, stamping, centrifugal casting, gel casting, extrusion, electrochemical deposition, screen and stencil printing, brush painting, and combinations of these methods.

The sensing layer thickness is preferably 0.1 nm to 500 nm, more preferably less than 100 nm, even more preferably less than 10 nm. The sensing layer is also preferably doped with catalysts and promoters to further enhance the selectivity of interaction or the kinetics of interaction, and to enhance the ability to detect the changes in the properties of the material composition. These secondary treatments of the sensing layer may enhance the performance of the sensing layer. Additionally, the sensing layer inside the pores can be porous or dense, conformal or tapered, planar or wavy, single layer or multilayered, or a combination of one or more of these.

Possible compositions of the sensing layer include but are not limited to organic, inorganic, metallic, alloy, ceramic, conducting polymer, non-conducting polymer, ion conducting, non-metallic, ceramic-ceramic composite, ceramic-polymer composite, ceramic-metal composite, metal-polymer composite, polymer-polymer composite, metal-metal composite, metal salts, metal complexes, bio-organisms, biologically active materials, biologically derived materials, biocomposites, or a combination of one or more of these. Illustrative compositions include but are not limited to doped or un-doped, stoichiometric or non-stoichiometric titanium oxide, barium titanate, strontium titanate, zinc oxide, indium oxide, zirconium oxide, tin oxide, antimony oxide, tungsten oxide, molybdenum oxide, tantalum oxide, cerium oxide, iron oxide, manganese oxide, rare earth oxides, binary and ternary complex oxides, lithium chloride, magnesium chloride, silicon carbide, bismuth telluride, gallium nitride, silicon, germanium, titanium boride, iron boride, zirconates, aluminates, tungstates, stannates, zincates, carbides, borates, hydrides, oxides, oxynitrides, oxycarbides, halides, silicates, phosphides, nitrides, chalcogenides, enzymes, nucleotides, antibodies, cells, and polymers.

Alternatively, the deposition of nanostructured sensing materials can be performed after the electroding and packaging of the sensor substrate. For example, selected properties of the sensing elements, such as its resistance is monitored in situ while the deposition process is conducted in the gas or liquid phase. This provides a feedback for controlling the deposition process and terminating the deposition as soon as desired value for the controlled parameter is achieved. The microheater can be used to locally control the deposition process temperature, thus effectively confining the deposition to the locally heated area, providing a means to terminate the deposition by switching off the microheater. Furthermore, analyte gases can be introduced in the reaction environment, providing performance feedback for the sensors under fabrication. Introducing analyte gases is preferably used for fabricating and testing multiple sensors or sensor arrays in a single production batch.

The local temperature control can be used to expand the processing capabilities and the productivity of atomic layer chemical vapor deposition of doped and multilayered sensing layers inside the pores. For example the microheater can control the temperature during the half-cycles comprising the binary reaction sequences of atomic layer deposition.

This, in turn, enables co-deposition of materials that require different deposition temperatures without having to adjust the temperature of the reaction chamber in every cycle.

The microheater can also be used to provide post-deposition forming and annealing of sensing materials at required temperatures.

After the sensor elements have been produced and packaged, they are calibrated. The calibration is preferably performed with a gas mixture whose composition varies in one of the desired species. The sensor signal value versus the concentration of the varying species is obtained. Such calibration data is then obtained for all species of interest.

Microsensor Operation

The sensors of the present invention, can be utilized to determine the composition and presence of vapors, gases and liquid analytes, as well as physical parameters of the gases, such as humidity, temperature, flow and pressure. The sensor element or array can be connected in a circuit to prepare a monitor capable of detecting changes in the property of the sensing layer. The sensor may be used as a disposable sensor or as a non-disposable sensor, as a regenerable or non-regenerable sensor, or as a continuous or cumulative sensor. The sensor element or sensor element array is preferably first exposed to the environment whose composition needs to be measured. The sensing mechanism can be based, for example, on resistance, capacitance, inductance, impedance, phase angle, loss factor, dissipation, breakdown voltage, electrical temperature coefficient of an electrical property, Nernst current, impedance associated with ion conducting, open circuit potential, electrochemical property, electronic property, magnetic property, thermal property, mechanical property, or optical property. For example, the impedance value is obtained and interpreted in light of the calibration data. The interpreted impedance then yields the desired composition information.

The microsensors and sensor arrays of the present invention have a very broad working temperature range and low thermal mass. This enables operation of the sensors at high temperature and high temperature scan rates. Operation modes include constant temperature control from ambient temperature to 1200° C., temperature steps, temperature ramp and soak, applying various temperature waveforms, including sine, square, triangular, arbitrary, and combinations of these modes. The operating temperature range is preferably ambient temperature to 1500° C., more preferably ambient temperature to 900° C.

The microheater temperature can be controlled by controlling the applied voltage, current or power. In temperature modulation mode the heater voltage scan rate can be up to and including 100V/s. In the sensor array operation, maintaining individual sensors with the same or different sensing elements at different temperatures provides a matrix of substantially simultaneous responses that can be used for analyzing complex gas mixtures.

Figure 9:
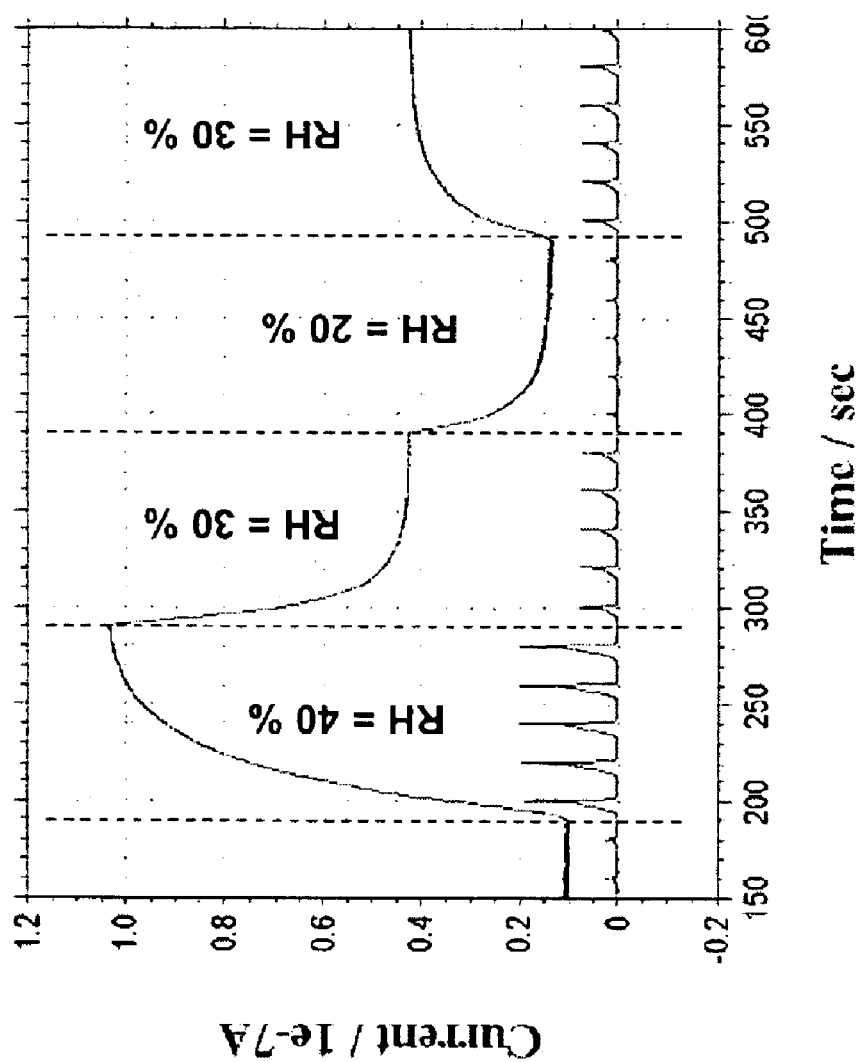
FIG. 9 presents response data of the humidity sensor of Example 5 in passive and temperature pulse modes.

Humidity measurements in the temperature pulse mode preferably include a "heater on" portion of the cycle—also called the desorption cycle—where the sensor is dehydrated to produce a dry sensing layer and/or sensor substrate for subsequent measurement. FIG. 9 presents current through the sensing element at a constant bias versus time for passive mode (heater not used) in the upper response curve in FIG. 9, and temperature pulse mode (heater on and off), shown by the lower response curve in FIG. 9. In FIG. 9, the vertical axis indicates current and the horizontal axis indicates elapsed time.

In the temperature pulse mode, the sensing layer readily adsorbs water during the "heater off" portion of the cycle, which is referred to as "adsorption" cycle. In the "heater on" portion of the cycle, the water molecules are desorbed from the sensing element, providing a reproducible current peak or set of current peaks indicated by the lower response curve in FIG. 9. By way of comparison with the passive-mode response curve in FIG. 9, while humidity measurements in the temperature pulse mode have improved base line, reproducibility, sensor response time (they are shorter), and detection limits (they are lower), among other measurement characteristics. Other analytes, such as hazardous gases, and physical parameters may be also measured in the temperature pulse mode. The passive mode provides highly sensitive, repeatable performance as well, and may be appropriate for certain applications.

A periodic on-board heating mode for the sensors of the present invention can be implemented by heating the sensor to the temperature from 5° C. above ambient to 500° C. and higher to regenerate the sensor after contamination, wetting or icing.

One of ordinary skill in the art will appreciate that particular sensor designs, sensing element properties, and operating mode are specifically designed to detect particular composition or physical parameter. Therefore, the choice of particular sensor designs and sensing layer properties may be applied for many applications. Furthermore, the methods discussed above can be utilized to prepare other devices and device arrays useful for photonic sensors, magnetic sensors, thermal sensors, electromagnetic field sensors, biomedical sensors, piezo sensors, bolometers, passive electronic components, interconnects, gas storage, energy storage, fuel cells, and other products.

The examples presented below are intended to more particularly describe the present invention, and are not intended to limit the scope of the invention.

EXAMPLE 1

Growth of Nanoporous Anodic Alumina Substrates

Pure (99.99% Al) aluminum foil was degreased in spectroscopic grade CC14 in an ultrasonic bath, and then rinsed in deionized water. The foil was immersed into the anodization bath with aluminum counterelectrodes. Anodic voltage was immediately applied to the aluminum substrate. The anodization bath comprised either sulfuric or oxalic acids, depending on the desired pore diameter. Electrolyte compositions, voltages, and temperatures for several specimens are listed in Table 1, as well as the resulting pore sizes.

TABLE 1

Processing conditions for growth of nanoporous anodic alumina

| pore diameter, nm | electrolyte composition, M (moles/liter) | anodization voltage, V | anodization temperature, ° C. |
|---|---|---|---|
| 70 | 0.25 M $H_2C_2O_4$ | 75 | 10 |
| 50 | 0.25 M $H_2C_2O_4$ | 54 | 20 |
| 25 | 0.25 M $H_2C_2O_4$ | 27 | 20 |
| 12 | 1.2 M $H_2SO_4$ | 15 | 20 |
| 9 | 1.2 M $H_2SO_4$ | 15 | 0 |
| 5 | 1.2 M $H_2SO_4$ | 7 | 20 |
| 5 | 1.2 M $H_2SO_4$ in MeOH | 15 | −20 |

EXAMPLE 2

Fabrication of Three-eElectrode Resistive Sensor Substrates by Anisotropic Etching Nanoporous AAO (Anodized Aluminum Oxide; a.k.a. anodic alumina) films were prepared on both sides of 5 cm×10 cm piece of Al foil as described in the Example 1, resulting in 70 nm pore diameter and 40 micrometer film thickness. A protective layer comprising aluminum and 5% by weight copper, that was 300 nm thick, was plasma sputtered onto both sides of the AAO to close the pores and prevent penetration of the photoresist inside the pores.

A standard positive photoresist was spin-coated at 4000 rpm and pre-baked at 120° C. for 1 minute. Both sides of the samples were exposed through a contact mask using a mask aligner, and developed in a standard developer solution. Resulting photoresist patterns were hard-baked at 160° for 1 hrs. Exposed areas of the Al/Cu layer were etched in the solution of 5% CuCl2 in 20% HCl to expose anodic alumina surfaces. Exposed AAO was etched in a solution of 200 g/l of CrO3 in 5M phosphoric acid at 95° C. for 5 minutes, or until the bottom Al surfaces appeared to dissolve off the oxide. Photoresist layers were stripped in commercial stripper solution. The remaining Al/Cu layers were etched and the sensor dies were separated from Al substrates in the solution of 5% CuCl2 in 20% HCl, rinsed and dried. SEM images of the resulting substrates are shown in FIG. 7. The width of the dual beam U-shape bridge-type sensing element 24 was 200 micrometers, and the length was 600 micrometers. The narrow gap 28 separating the beams and the substrate was machined to thermally isolate the microheater, and avoid shorting the microheater and the sensing electrodes during the sputtering through low resolution shadow masks.

Electrodes were prepared by plasma sputtering of Pt through a set of shadow masks, the final thickness for the contact pads and traces was 300 nm, 100 nm for sensing electrodes and 150 nm for the microheater. A thin (5 nm) tantalum layer was sputtered prior to the platinum sputtering to increase the adhesion of electrodes. The sensors were soldered onto a TO-5 header with Sn—Ag solder. The resistance of the microheater was 25 Ω. This type of microheater on alumina substrate was able to sustain active heating up to 900° C., which is at least 250° C. higher then existing Si-based microheaters. The power required to maintain the sensing element at 500° C. was about 25 mW.

EXAMPLE 3

Fabrication of Three-electrode Sensor Substrates by Localized Anodization

Nanoporous AAO films were prepared on both sides of 5 cm×10 cm piece of Al foil as described in the Example 1 for 70 nm pore diameter, except the film thickness was limited to 0.25 μm. A standard positive photoresist was spin-coated at 4000 rpm without a protective layer and pre-baked at 120° C. for 1 minute. Both sides of the samples were exposed through a contact mask using a mask aligner, and developed in a standard developer solution. Resulting photoresist pattern was hard-baked at 160° C. for 1 hour. The samples were inserted into a anodization bath, and a second anodization was performed at 75V in exposed areas until additional 40 μm of AAO was grown. At the end of the anodization, the samples were polarized at −100V in the anodization solution until gas evolution was observed in the exposed areas. This procedure opened the barrier layer. The photoresist layers were then stripped in the commercial stripper solution. The sensor dies were separated from Al substrates in the solution of 5% CuCl2 in 20% HCl, rinsed and dried. SEM images of the resulting substrates are shown in FIG. 8. The width of the monolithic bridge-type sensing element 24 was 0.7 mm, and the length was 1.4 mm. This size reduced the shorting of the microheaters and the sensing electrodes deposited on the opposite faces of the die by plasma sputtering through shadow masks.

The thickness of the contact pads and conductive traces was 500 nm. Central part of the sensing electrodes was 100 nm, and the microheater thickness was 150 nm. A thin (5 nm) titanium layer was sputtered prior to platinum sputtering in order to increase the adhesion of electrodes. The sensors were soldered onto a TO-5 header with Sn—Ag solder. The resistance of the microheater was 12 Ω. This type of microheater on alumina substrate was able to sustain active heating for up to 1200° C., which is at least 550° C. higher then existing Si-based microheaters. The power required to maintain the sensing element at 500° C. was 200 mW.

EXAMPLE 4

Fabrication of Two-electrode Combustible Gas Sensor Substrates

Anodic alumina films were formed as described in Example 1, with pore diameter of 40 nm and microfabrication was performed similar to that in Example 2, except the photolithographic contact mask was of a different design which contained dual platinum microheater elements deposited onto one side of the sensor substrate. Power consumption of this microsensor substrate was 42 mW at 500° C.

The sensors were soldered onto a TO-5 header with Sn—Ag solder. Long term testing of stability of dual microheaters at 520° C. revealed resistance drift of 1.8 Ohm/month in constant current mode, 0.28 Ohm/month in constant power mode, and only 0.07 Ohm per month in the current pulse mode at 10% duty cycle, which is superior to existing combustible gas microsensors. The resistance of Pt thin film microheaters was shown to depend on temperature. These data were used to calculate the temperature coefficient of resistivity (TCR), which were in the range from 0.00265 to 0.0028, slightly lower than Pt wire TCR (0.0036). Therefore, thin film platinum microheaters could be used as temperature detectors.

EXAMPLE 5

Resistive Humidity Sensor from Bare Alumina

Anodic alumina films were formed in oxalic acid electrolyte as described in Example 1, with pore diameter of 40 nm and thickness of 40 micrometers. Microfabrication was performed similar to that in Example 3, except that prior to the deposition of sensing electrodes and microheaters 50% of the substrates were annealed to 850° C. for 1 hour. No additional deposition of sensing materials was performed.

Testing of these sensors was performed at different temperatures and humidity levels. The testing was performed using two test profiles after dehydration of the sensor at 300° C. for 30 seconds: (1) passive mode—heater was turned off; (2) temperature pulse mode—heater temperature was continuously pulsed from ambient (0V) to 200° C. (1.2 V) with 10 second pulse length. The time to reach 95% of the temperature set point was only 1.7 seconds. The sensor signal was the current through the sensing element at a constant bias (10V), as shown in FIG. 9.

The prototypes that were prepared from annealed substrates showed best performance during this testing. It was observed, as shown in FIG. 9, that the response time to change in humidity in passive mode was minutes. On the contrary, only one cycle was needed to saturate the response in temperature pulse mode. Furthermore, because during each heating half-cycle the sensor was dehydrated, the base line in a pulse mode was significantly lower. The water vapor begins on a fresh dry alumina surface during the each heater off half-cycle. Both desorption and adsorption half-cycles provide very reproducible and stable signals. This led to the increase in sensitivity to 40% RH from 0.9 in passive mode to 1.0 in the pulse mode.

Annealed sensors were also tested in a temperature pulse mode at low temperatures (down to −15° C.), and exhibited response times of less than the time needed for one cycle, and sensitivity of about 0.98 to 50% RH.

EXAMPLE 6

Modification of the Resistance and the Response Time of the Resistive Humidity Sensor Humidity sensors were fabricated similar to the Example 5, except sensors were modified with zinc oxide as conductive media and hydrophilic metal salts, such as lithium chloride, to decrease the sensor resistance and to increase the sensitivity.

Zinc oxide was deposited by atomic layer deposition from dimethyl zinc and water at 177° C. The thickness of the ZnO films was proportional to the number of cycles performed. The thickness of the deposited ZnO was 3 nm. This was found to decrease the sensor base resistance from ~10¹⁰ Ω to about ~10⁷ Ω, which is more suitable for practical resistive transducers.

Lithium chloride was deposited by impregnation from aqueous and alcohol solutions at concentrations from 1% to 25%. Testing of the resulting sensors in the temperature pulse mode showed lower resistivity, significantly higher sensitivity and decreased response time.

EXAMPLE 7

Combustible Gas Sensor

Combustible gas sensor substrates were fabricated as described in the Example 4. To produce combustible gas sensors, one of the two sensing elements was brush-coated with aqueous solutions of platinum and palladium salts in nitric acid, followed by on-board heating to dry the solutions and to decompose the salts to form catalytic nanoparticles on alumina surfaces.

Such sensors were operated in one of the following modes: constant voltage, pulse voltage, constant current and pulse current at work temperature from ambient temperatures to 600° C. When the combustible gas reached a sensing element maintained at proper temperature, catalytic combustion occurred and the sensor temperature increased, resulting in increased microheater resistance. The result in the voltage control mode was decreased current, and in the current control mode—increased voltage, which were measured in a bridge circuit with the blank sensor (no catalyst) as the reference.

These sensors were tested with several combustible gases, such as methane, ethanol and hydrogen. Excellent performance was observed in detecting methane as shown in Table 2:

TABLE 2

Performance of combustible gas sensor

| Parameter | Value |
| --- | --- |
| Base operating temperature | 500° C. (in air) |
| Power consumption in air, no pulse | 42 mW |
| Current draw (in air) | 37 ± 3.5 mA |
| Hot resistance (in air) | 25–30 Ω |
| Hot resistance stability (100 mV net span basis) | 0.85 Ω/yr in pulse mode<br>3.4 Ω/yr in constant power mode |
| Net span in 2.5% methane (constant current mode) | 90–120 mV |
| Cycling test | >50,000 cycles from 0 mA to operating current |

These sensors showed net signal up to 350 mV to 2.5% of CH4 in air at temperatures above 350° C. A direct correlation was found between specific surface area of the AAO substrate and the sensitivity of the sensor. Catalyst deactivation, which sometimes took place at lower temperature, could be reversed using a short high temperature pulse.

Furthermore, capability to discriminate between hydrogen and methane was observed with cyclic sweeps of the microheater voltage: increasing sweep rate led to a decreasing signal in methane, while the signal in hydrogen increased.

EXAMPLE 8

Resistive $SnO_2$ Sensor Prepared by Wet Chemical Route

Sensor substrates were prepared similar to Example 3. Tin oxide deposition was performed by brush- and dip-coating from 10% solution of Sn(i-PrO)4 in isopropanol (reagent grade, Aldrich). It was found to have excellent capability for impregnating the pores of anodic alumina, with fast gelation following solvent evaporation. The variables that affect the deposition of tin oxide from this system were: (1) application technique and number of applications; (2) surface area and wettability of the substrate; and (3) solvent evaporation rate, which was increased by on-board heating.

SnO2 deposition was monitored by measuring sensor current vs. microheater voltage during the application of the precursor solution and drying. Application of Sn(I—PrO)4 solution results in a significant current increase during the first heater voltage (temperature) ramp, followed by reduction of current in the next temperature ramp due to solvent evaporation and conversion into tin oxide. Each consecutive application resulted in further decrease in the sensor base resistance. After the final application of the tin precursor, the upper temperature limit was gradually increased. As the temperature increased, new stages of conversion were observed as indicated by reduction of the current peaks followed by stabilization. At 500° C., the sensor was stabilized by cycling the heater voltage several times until the sensor current became reproducible.

Figure 10:
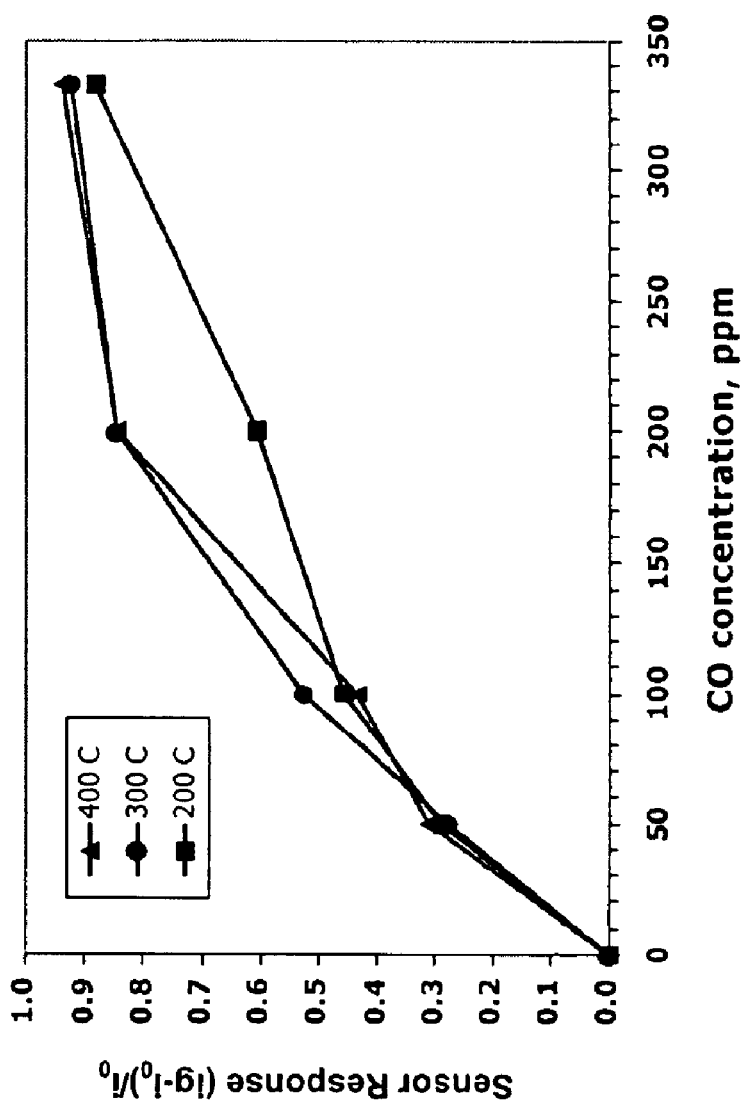
FIG. 10 presents the sensitivity data of the sensor of Example 8 to carbon monoxide.

Sensors were tested in different operation modes and promising performance was demonstrated for the detection and discrimination of toxic gases of interest in air quality monitoring, specifically formaldehyde, VOCs (a.k.a. Volatile Organic Compounds), and carbon monoxide. The results are shown in FIG. 10, which presents sensor response to carbon monoxide versus its concentration at different temperatures. In FIG. 10, the vertical axis indicates sensor response expressed in terms of a dimensionless value indicating a difference between the response current in presence of CO gas (Ig) and the sensor response current in the absence of the gas (I0), normalized by dividing by I0. Interestingly, both the sensitivity and its dependence on the temperature are very different for these gases. For example, at 400° C. for 100 ppm, a tested sensor's sensitivity decreases in the following sequence:

EtOH(~6)>HCOH(~3.2)>CO(0.5)>>H$_2$.

It should be noted, that the response to CO barely depends on the temperature in the 200–400° C. range as shown in FIG. 10, while both HCOH and EtOH sensitivities are a strong function of operating temperature. This feature can be further utilized in the design and operation of sensor arrays, enabling discrimination of specific gas species of interest.

EXAMPLE 9

Resistive ZnO Sensor Prepared by Gas-Phase Route

Sensor substrates were prepared similar to Example 3. Zinc oxide was deposited similar to the Example 6. The thickness of the deposited ZnO was 20 nm. This was found to decrease the sensor base resistance from about 1010 Ω to about 104 Ω.

Figure 11:
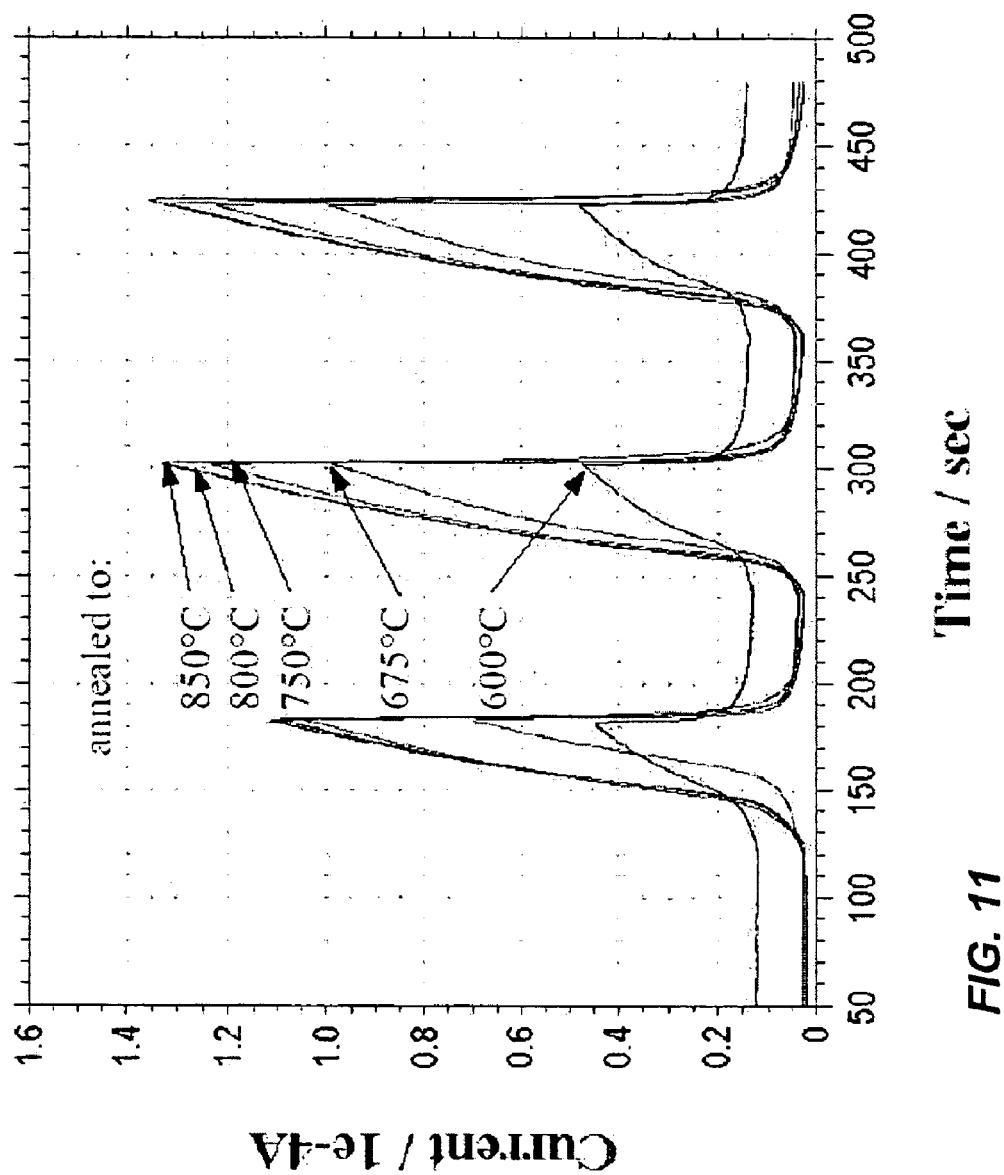
FIG. 11 presents the effect of on-board annealing on the response of the resistive ZnO sensor of Example 9 to 300 ppm HCOH at 400° C.

The sensors had a promising response to HCOH. FIG. 11 shows current through the sensing element at a constant bias of 10 V versus time for three 100 ppm step-changes of formaldehyde. On-board annealing up to 850° C., as shown in FIG. 11, was found to affect and improve the sensor performance. FIG. 11 illustrates a response curve similar to that shown in FIG. 9 for a device that was annealed at different temperatures indicated in FIG. 11. Annealing was performed by ramping the heater voltage to the value, corresponding to heater temperatures from 600° C. (2.6 V) to 850° C. (3.7V). The baseline decreased significantly, and the response increased, resulting in the sensitivity improvement by a factor of 20.

EXAMPLE 10

Resistive TiO$_2$ Sensor Prepared by Sol-gel Route

Sensor substrates were prepared similar to Example 2, except that after anodization a short (3 to 10 seconds) cathodic polarization (−50 to −200 V) was applied to the anodic alumina film still attached to Al foil in 3M phosphoric acid to open the barrier layer. Titanium oxide was deposited via sol-gel route using an original approach for uniform deposition on the high aspect pore walls without clogging the pore entrance. Solutions of 0.1 to 10% by weight of titanium isopropoxide in isopropanol with pH from 3 to 4 maintained by hydrochloric acid, which were aged to obtain desired viscosity, were applied by filtering small aliquots through the AAO substrate sandwiched between the two circular membranes. The pore diameter of the bottom one was smaller, and the top one—larger then that for microsensor substrate to enable effective filtering through the microsensor substrate. After filtering sensor substrates were allowed to dry. This procedure, when repeated several times (from 2 to 100), depending on the pore diameter, resulted in very uniform coatings of titania on the pore walls, while the top surface of the sample was free of the excess deposit.

Performance of sensing elements from nanostructured titania inside the pores of anodic alumina were thoroughly evaluated in passive and temperature pulse modes. Significantly higher sensor response and better S/N to oxygen was measured with produced prototype, than with bulk ceramic sensors: nanostructured sensors showed noticeable response to 1% oxygen at temperature as low as 650° C. Response time for the step change in oxygen concentration was also significantly improved.

Furthermore, in the temperature pulse mode, the response time and the signal stability was further improved. Response rate of the microsensor in active mode, determined from the rise time after oxygen reached the sensor, was well below 1 s, which is significantly shorter then that of the bulk sensors. This shows strong promise for real-time applications.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What we claim is:

1. A method for preparing a device comprising:
   providing a substrate;
   depositing a layer comprising metal on the substrate;
   processing the deposited layer into a substance comprising substantially parallel nanoscale pores;
   depositing a substance of first composition in the nanoscale pores; and
   providing at least one additional layer of second composition substantially perpendicular to the substance deposited in the nanoscale pores.

2. The method of claim 1, wherein the substrate comprises silicon wafer.

3. The method of claim 1, wherein the substrate comprises glass.

4. The method of claim 1, wherein the substrate comprises polymer.

5. The method of claim 1, wherein the substrate comprises metal.

6. The method of claim 1, wherein the layer comprising metal comprises aluminum.

7. The method of claim 1, wherein the substance of first composition comprises nanotubes or nanowires.

8. The method of claim 1, wherein the act of depositing a substance of first composition is followed by dissolution of the substance comprising substantially parallel nanoscale pores.

9. The method of claim 1, wherein the device comprises copper.

10. The method of claim 1, wherein the act of depositing a substance of first composition comprises one or more actions selected from the group consisting of spin coating, dip coating, spray coating, solution impregnation, sputtering, reactive sputtering, physical vapor deposition, chemical vapor deposition, atomic layer deposition, ion beam, e-beam deposition, molecular beam epitaxy, laser deposition, plasma deposition, electrophoretic deposition, magnetophoretic deposition, thermophoretic deposition, stamping, centrifugal casting, gel casting, extrusion, electrochemical deposition, printing and painting.

11. The method of claim 1, wherein the substance of first composition comprises a substance selected from the group—organic, inorganic, metal, alloy, ceramic, polymer, ion conducting, non-metallic, composite, metal salts, metal complexes, bio-organisms, biologically active materials, biologically derived materials and biocomposites.

12. The method of claim 1, wherein the substance of first composition comprises a substance selected from—titanium oxide, barium titanate, strontium titanate, zinc oxide, indium oxide, zirconium oxide, tin oxide, antimony oxide, tungsten oxide, molybdenum oxide, tantalum oxide, cerium oxide, iron oxide, manganesa oxide, rare earth oxides, binary and ternary complex oxides, lithium chloride, magnesium chloride, silicon carbide, bismuth telluride, gallium nitride, silicon, germanium, titanium boride, iron bonds, zirconates, eluminates, tungatates, stannotes, zincates, carbides, borutes, hydrides, oxides, oxynitrides, oxycarbides, halides, silicates, phosphides, nitrides, chalcogenides, enzymes, nucleotides, antibodies, cells, and polymers.

13. The method of claim 1 further comprising patterning the layer comprising metal using a mask.

14. The method of claim 1 wherein the act of depositing or processing includes photolithography.

15. The method of claim 1 wherein the device comprises a sensing device.

16. The method of claim 1 wherein the device comprises an electromagnetic device.

17. The method of claim 1 wherein the device comprises an electronic device.

18. The method of claim 1 wherein the device comprises an interconnect.

19. A method for preparing a device comprising:
providing a wafer comprising silicon;
depositing a layer on the wafer;
processing the deposited layer Into a substance comprising substantially parallel nanoscale pores;
preparing nanotubes or nanowires in the nanoscale pores; and
providing at least one additional layer of second composition substantially perpendicular to the nanotubes.

* * * * *